(12) United States Patent
Kabala et al.

(10) Patent No.: US 11,446,079 B2
(45) Date of Patent: Sep. 20, 2022

(54) SURGICAL INSTRUMENTS INCORPORATING ULTRASONIC AND ELECTROSURGICAL FUNCTIONALITY

(71) Applicant: Covidien LP, Mansfield, MA (US)

(72) Inventors: Rachael L. Kabala, Fort Collins, CO (US); Anthony B. Ross, Boulder, CO (US); David J. Van Tol, Boulder, CO (US); Robert B. Stoddard, Steamboat Springs, CO (US); Robert B. Smith, Loveland, CO (US)

(73) Assignee: Covidien LP, Mansfield, MA (US)

( * ) Notice: Subject to any disclaimer, the term of this patent is extended or adjusted under 35 U.S.C. 154(b) by 677 days.

(21) Appl. No.: 16/238,668

(22) Filed: Jan. 3, 2019

(65) Prior Publication Data

US 2019/0216530 A1 Jul. 18, 2019

Related U.S. Application Data

(60) Provisional application No. 62/618,277, filed on Jan. 17, 2018, provisional application No. 62/618,241, (Continued)

(51) Int. Cl.
*A61B 18/12* (2006.01)
*A61B 18/14* (2006.01)
(Continued)

(52) U.S. Cl.
CPC .. *A61B 18/1445* (2013.01); *A61B 17/320092* (2013.01); *A61B 2017/320075* (2017.08);
(Continued)

(58) Field of Classification Search
CPC .... A61B 17/320092; A61B 17/320094; A61B 18/1445; A61B 2017/320095; A61B 2018/1452; A61B 2018/1455
See application file for complete search history.

(56) References Cited

U.S. PATENT DOCUMENTS

| 5,190,517 A | 3/1993 | Zieve et al. |
| 5,312,329 A | 5/1994 | Beaty et al. |

(Continued)

FOREIGN PATENT DOCUMENTS

| EP | 2322111 A1 | 5/2011 |
| EP | 2474280 A1 | 7/2012 |

(Continued)

OTHER PUBLICATIONS

Extended European Search Report issued in corresponding European Application No. 19152030.3 dated Apr. 10, 2019, 8 pages.

(Continued)

*Primary Examiner* — Daniel W Fowler

(74) *Attorney, Agent, or Firm* — Carter, DeLuca & Farrell LLP

(57) ABSTRACT

A surgical instrument end effector assembly includes a first jaw member and a second jaw member. The second jaw member includes an ultrasonic blade body and first and second electrodes disposed on either side of the ultrasonic blade body and extending longitudinally along a majority of a length of the ultrasonic blade body. The ultrasonic blade body is adapted to receive ultrasonic energy from an ultrasonic waveguide. The first and second electrodes taper in width proximally to distally and are adapted to connect to a source of electrosurgical energy. The first jaw member is movable relative to the second jaw member between a spaced-apart position and an approximated position for grasping tissue therebetween.

18 Claims, 7 Drawing Sheets

Related U.S. Application Data filed on Jan. 17, 2018, provisional application No. 62/618,292, filed on Jan. 17, 2018, provisional application No. 62/618,402, filed on Jan. 17, 2018.

(51) Int. Cl.
 *A61B 17/32* (2006.01)
 *A61B 18/00* (2006.01)

(52) U.S. Cl.
 CPC ............ *A61B 2017/320094* (2017.08); *A61B 2017/320095* (2017.08); *A61B 2018/0016* (2013.01); *A61B 2018/0063* (2013.01); *A61B 2018/00083* (2013.01); *A61B 2018/0094* (2013.01); *A61B 2018/00922* (2013.01); *A61B 2018/00994* (2013.01); *A61B 2018/1452* (2013.01); *A61B 2018/1455* (2013.01); *A61B 2018/1467* (2013.01)

(56) References Cited

U.S. PATENT DOCUMENTS

| | | | |
|---|---|---|---|
| 5,443,463 | A | 8/1995 | Stern et al. |
| 6,251,110 | B1 | 6/2001 | Wampler |
| 6,257,241 | B1 | 7/2001 | Wampler |
| 6,416,486 | B1 | 7/2002 | Wampler |
| 6,562,032 | B1 | 5/2003 | Ellman et al. |
| 6,736,814 | B2 | 5/2004 | Manna et al. |
| 7,717,913 | B2 | 5/2010 | Novak et al. |
| 8,773,001 | B2 | 7/2014 | Wiener et al. |
| 9,700,366 | B2 | 7/2017 | Paulus |
| 2002/0107517 | A1* | 8/2002 | Witt .................. A61B 18/1442 606/50 |
| 2007/0173872 | A1 | 7/2007 | Neuenfeldt |
| 2010/0145335 | A1 | 6/2010 | Johnson et al. |
| 2011/0015627 | A1* | 1/2011 | DiNardo ............ A61B 18/1445 606/34 |
| 2012/0150176 | A1 | 6/2012 | Weizman |
| 2014/0135804 | A1 | 5/2014 | Weisenburgh, II et al. |
| 2014/0330271 | A1 | 11/2014 | Dietz et al. |
| 2015/0088128 | A1* | 3/2015 | Couture ............. A61B 18/1445 606/42 |
| 2015/0141981 | A1* | 5/2015 | Price .................. A61B 18/1445 606/38 |
| 2015/0164533 | A1 | 6/2015 | Felder et al. |
| 2015/0182251 | A1 | 7/2015 | Messerly et al. |
| 2016/0038220 | A1 | 2/2016 | Twomey |
| 2017/0007317 | A1 | 1/2017 | Allen, IV et al. |
| 2017/0105754 | A1 | 4/2017 | Boudreaux et al. |
| 2017/0164973 | A1 | 6/2017 | Lesko et al. |
| 2017/0202609 | A1 | 7/2017 | Shelton, IV et al. |
| 2018/0125569 | A1* | 5/2018 | Vaders ................... B29C 70/76 |

FOREIGN PATENT DOCUMENTS

| | | | |
|---|---|---|---|
| EP | 2583633 | A1 | 4/2013 |
| EP | 2829245 | A1 | 1/2015 |
| EP | 2946737 | A1 | 11/2015 |
| EP | 3117790 | A1 | 1/2017 |
| WO | 9517855 | A1 | 7/1995 |
| WO | 2017100423 | A2 | 6/2017 |
| WO | 2017123837 | A2 | 7/2017 |

OTHER PUBLICATIONS

Partial European Search Report issued in corresponding European Application No. 19152028.7 dated Apr. 12, 2019, 12 pages.
Extended European Search Report issued in corresponding European Application No. 20201742.2 dated Feb. 10, 2021, 8 pages.
Communication Pursuant to Article 94(3) EPC issued in corresponding European Application No. 19152028.7 dated May 7, 2021, 5 pages.
Extended European Search Report issued in corresponding European Application No. 20195714.9 dated Dec. 21, 2020, 8 pages.
Extended European Search Report issued in European Application No. 19152026.1 dated Jun. 28, 2019, 6 pages.
Extended European Search Report issued in European Application No. 19152133.5 dated Jun. 28, 2019, 6 pages.

* cited by examiner

SURGICAL INSTRUMENTS INCORPORATING ULTRASONIC AND ELECTROSURGICAL FUNCTIONALITY

The present application claims the benefit of and priority to U.S. Provisional Application Ser. Nos. 62/618,241, 62/618,277, 62/618,292, and 62/618,402, all of which were filed on Jan. 17, 2018. The present application is related to U.S. patent application Ser. Nos. 16/238,600, 16/238,754, and 16/238,812, all of which were filed on Jan. 3, 2019. The entire contents of each of the above applications are hereby incorporated herein by reference.

BACKGROUND

1. Technical Field

The present disclosure relates to energy-based surgical instruments and, more particularly, to surgical instruments having end effector assemblies incorporating ultrasonic and electrosurgical functionality to facilitate treating, e.g., sealing and/or dissecting tissue.

2. Discussion of Related Art

Ultrasonic surgical devices are used in many surgical procedures. An ultrasonic surgical device may include, for example, an ultrasonic blade and a clamp mechanism to enable clamping tissue against the blade. Ultrasonic energy transmitted to the blade causes the blade to vibrate at very high frequencies (e.g., 55,500 times per second), which allows for heating tissue to treat tissue clamped against or otherwise in contact with the blade.

Electrosurgical devices are also used in many surgical procedures. An electrosurgical device may include, for example, opposing jaw members operable to clamp tissue therebetween and conduct energy, e.g., RF energy, through clamped tissue to treat tissue.

Devices that combine ultrasonic and electrosurgical energy into a single multi-functional device are known, but may not leverage the strengths of both technologies effectively. In particular, existing devices may have end effectors that are not optimized for the combined use of ultrasonic and electrosurgical energy.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a surgical instrument including an end effector assembly having first and second jaw members. The second jaw member includes an ultrasonic blade body and first and second electrodes disposed on either side of the ultrasonic blade body and extending longitudinally along a majority of a length of the ultrasonic blade body. The ultrasonic blade body is adapted to receive ultrasonic energy from an ultrasonic waveguide. The first and second electrodes taper in width proximally to distally and are adapted to connect to a source of electrosurgical energy. The first jaw member is movable relative to the second jaw member between a spaced-apart position and an approximated position for grasping tissue therebetween.

In an aspect of the present disclosure, the first and second electrodes are electrically-isolated from one another and energizable to different potentials for conducting electrosurgical energy therebetween.

In another aspect of the present disclosure, the first and second electrodes are electrically-coupled to one another and configured to conduct energy from the first and second electrodes to the first jaw member.

In yet another aspect of the present disclosure, the first jaw member includes a jaw liner disposed thereon and positioned to oppose the ultrasonic blade body of the second jaw member.

In still another aspect of the present disclosure, the first jaw member includes first and second electrodes positioned to oppose the first and second electrodes, respectively, of the second jaw member. The first and second electrodes of the first jaw member may be electrically-isolated from one another and energizable to different potentials for conducting electrosurgical energy therebetween, and/or the first and second electrodes of the first jaw member and the first and second electrodes of the second jaw member may be energizable to different potentials for conducting electrosurgical energy therebetween.

In still yet another aspect of the present disclosure, the surgical instrument further includes a housing, a shaft extending distally from the housing, and an ultrasonic waveguide extending through the shaft. The end effector assembly is supported at a distal end portion of the shaft.

In another aspect of the present disclosure, a trigger is operably associated with the housing and coupled to the first jaw member. The trigger is selectively actuatable to move the first jaw member relative to the second jaw member between the spaced-apart position and the approximated position.

In still another aspect of the present disclosure, an activation button is disposed on the housing. The activation button is selectively activatable to supply electrosurgical energy and/or ultrasonic energy to the end effector assembly.

Another surgical instrument provided in accordance with aspects of the present disclosure includes an end effector assembly having first and second jaw members. The first jaw member includes a jaw body and first and second electrodes. The jaw body defines an electrically-insulative inwardly-facing tissue-contacting surface and an outwardly facing surface. The first and second electrodes are disposed on the outwardly facing surface of the jaw body and adapted to connect to a source of electrosurgical energy. The second jaw member includes an ultrasonic blade body adapted to connect to an ultrasonic waveguide and adapted to connect to a source of electrosurgical energy. The first jaw member is movable relative to the second jaw member between a spaced-apart position and an approximated position for grasping tissue between the tissue-contacting surface of the first jaw member and the ultrasonic blade body of the second jaw member.

In an aspect of the present disclosure, the jaw body of the first jaw member is formed from an insulative material. Additionally or alternatively, the jaw body of the first jaw member is formed from a compliant material.

In another aspect of the present disclosure, the tissue-contacting surface of the jaw body of the first jaw member is shaped complementary to an opposite surface of the ultrasonic blade body of the second jaw member. The tissue-contacting surface of the jaw body of the first jaw member may define an arcuate configuration.

In still yet another aspect of the present disclosure, the surgical instrument further includes a housing, a shaft extending distally from the housing, and an ultrasonic waveguide extending through the shaft. The end effector assembly is supported at a distal end portion of the shaft.

In another aspect of the present disclosure, a trigger is operably associated with the housing and coupled to the first jaw member. The trigger is selectively actuatable to move the first jaw member relative to the second jaw member between the spaced-apart position and the approximated position.

In yet another aspect of the present disclosure, an activation button is disposed on the housing. The activation button is selectively activatable to supply electrosurgical energy and/or ultrasonic energy to the end effector assembly.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 1:
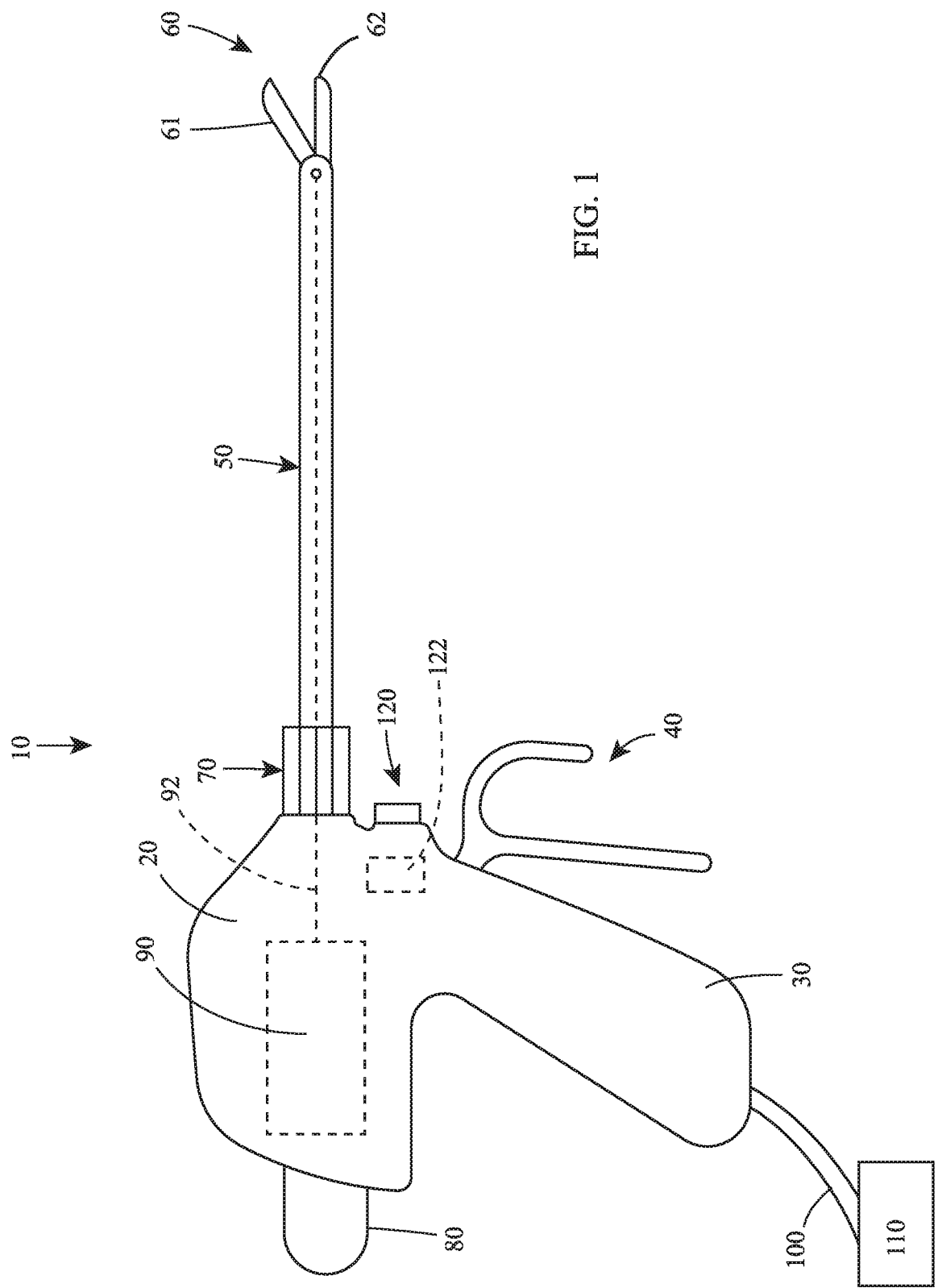
FIG. 1 is a side view of a surgical instrument exemplifying the aspects and features of the present disclosure.

Referring generally to FIG. 1, a combined electrosurgical, e.g., RF, and ultrasonic surgical instrument exemplifying the aspects and features of the present disclosure is shown and generally identified by reference numeral 10. For the purposes herein, surgical instrument 10 is generally described. Aspects and features of surgical instrument 10 not germane to the understanding of the present disclosure are omitted to avoid obscuring the aspects and features of the present disclosure in unnecessary detail.

Surgical instrument 10 generally includes a housing 20, a handle 30, a trigger 40, an elongated shaft 50, an end effector assembly 60, a rotating assembly 70, an ultrasonic transducer 90, a cable 100 coupled to a surgical generator 110, and an activation switch 120. Activation switch 120 selectively activates a supply of electrosurgical energy from generator 110 to end effector 60 for treating tissue in an electrosurgical energy mode and selectively activates a supply of ultrasonic energy from ultrasonic transducer 90 (powered by generator 110) to end effector assembly 60 for treating tissue in an ultrasonic energy mode. To accomplish this, a switch box 122 disposed within housing 20 and coupled to activation switch 120 and/or generator 110 may be provided to determine the mode of surgical instrument 10 and enable the supply of the appropriate energy depending upon the mode. Alternatively, separate switches may be provided for each mode. Further, as an alternative to a separate generator 110, a generator and battery may be incorporated on or within housing 20 such that surgical instrument 10 operates as a cordless device.

With continued reference to FIG. 1, elongated shaft 50 of surgical instrument 10 extends distally from housing 20 and supports end effector assembly 60 at a distal end portion of elongated shaft 50. End effector assembly 60 is disposed at the distal end portion of elongated shaft 50 and includes first and second jaw members 61, 62, respectively, that cooperate to clamp and treat tissue, as described in further detail below. Rotating assembly 70 enables the selective rotation of elongated shaft 50 and, thus, end effector assembly 60 relative to housing 20.

Handle 30 is integrally associated with housing 20 for clamping and/or handling surgical instrument 10. Trigger 40 is movable relative to handle 30 from an initial position to an actuated position. Trigger 40 is operably coupled to a drive assembly (not shown) that mechanically imparts movement to end effector assembly 60. More specifically, actuation of trigger 40 causes first jaw member 61 to pivot relative to second jaw member 62 from a spaced-apart position to an approximated position to clamp tissue therebetween.

End effector assembly 60, as noted above, includes first and second jaw members 61, 62. Generally, in an ultrasonic mode, when activation switch 120 is activated, second jaw member 62 serves as an ultrasonic blade that is acoustically coupled to ultrasonic transducer 90 via a waveguide 92 to enable transmission of ultrasonic energy from ultrasonic transducer 90, along waveguide 92, to second jaw member 62 for treating tissue. In an electrosurgical mode, when activation switch 120 is activated, electrodes on one or both of the jaw members 61, 62 are energized to enable the conduction of electrosurgical energy through tissue clamped between jaw members 61, 62 to treat tissue. Various embodiments of end effector configurations suitable for use with surgical instrument 10 for the above purposes are described in detail below with reference to FIGS. 2-5. To the extent consistent, any of the aspects and features of the embodiments detailed below may be incorporated into any of the other embodiments.

Figure 2:
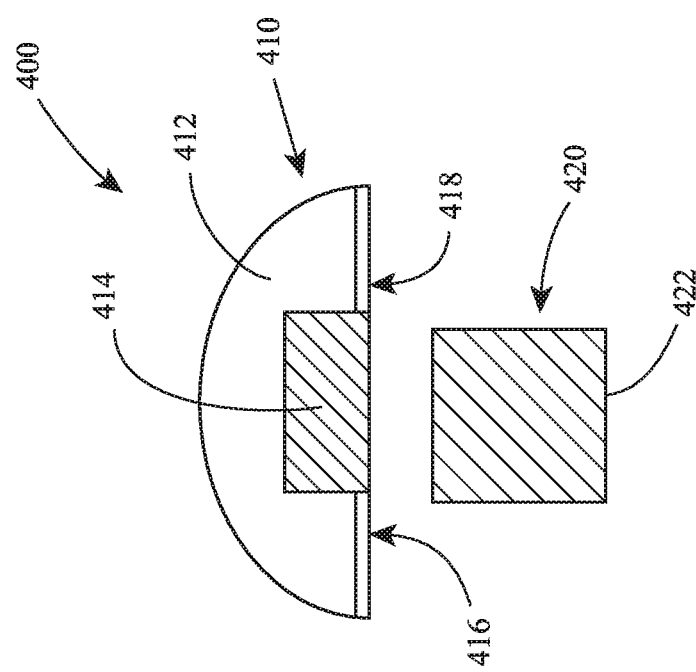
FIG. 2 is a transverse, cross-sectional view of an end effector assembly configured for use with the surgical instrument of FIG. 1.

Referring now to FIG. 2, in conjunction with FIG. 1, another end effector assembly 400 of the present disclosure is shown. End effector assembly 400 generally includes a first jaw member 410 and a second jaw member 420. First jaw member 410 includes a jaw body 412 having a jaw liner 414 and first and second electrodes 416, 418, disposed thereon. Jaw liner 414 may be formed from an insulative, compliant material, e.g., polytetraflouroethylene (PTFE), and is positioned to oppose jaw member 420, which is an ultrasonic blade body 422. First and second electrodes 416, 418 are positioned transversely on first jaw member 410 with jaw liner 414 disposed therebetween and are electrically isolated to enable conduction of electrosurgical energy therebetween, transversely between jaw members 410, 420. First and second electrodes 416, 418 may each be electrically coupled to generator 110 and activation switch 120, e.g., via one or more lead wires (not shown) extending through cable 100, housing 20, and elongated shaft 50.

In use, electrosurgical energy delivery and ultrasonic energy delivery are activated simultaneously, in staggered but overlapping temporal relation, or consecutively. More specifically, first and second electrodes 416, 418 are energized to different potentials to conduct electrosurgical energy transversely therebetween and through tissue clamped between jaw members 410, 420, while ultrasonic energy is transmitted to ultrasonic blade body 422, which remains electrically neutral so as not to interfere with the conduction of energy between electrodes 416, 418, via waveguide 92 for transmission to tissue clamped between ultrasonic blade body 422 and jaw liner 414.

Figure 3A:
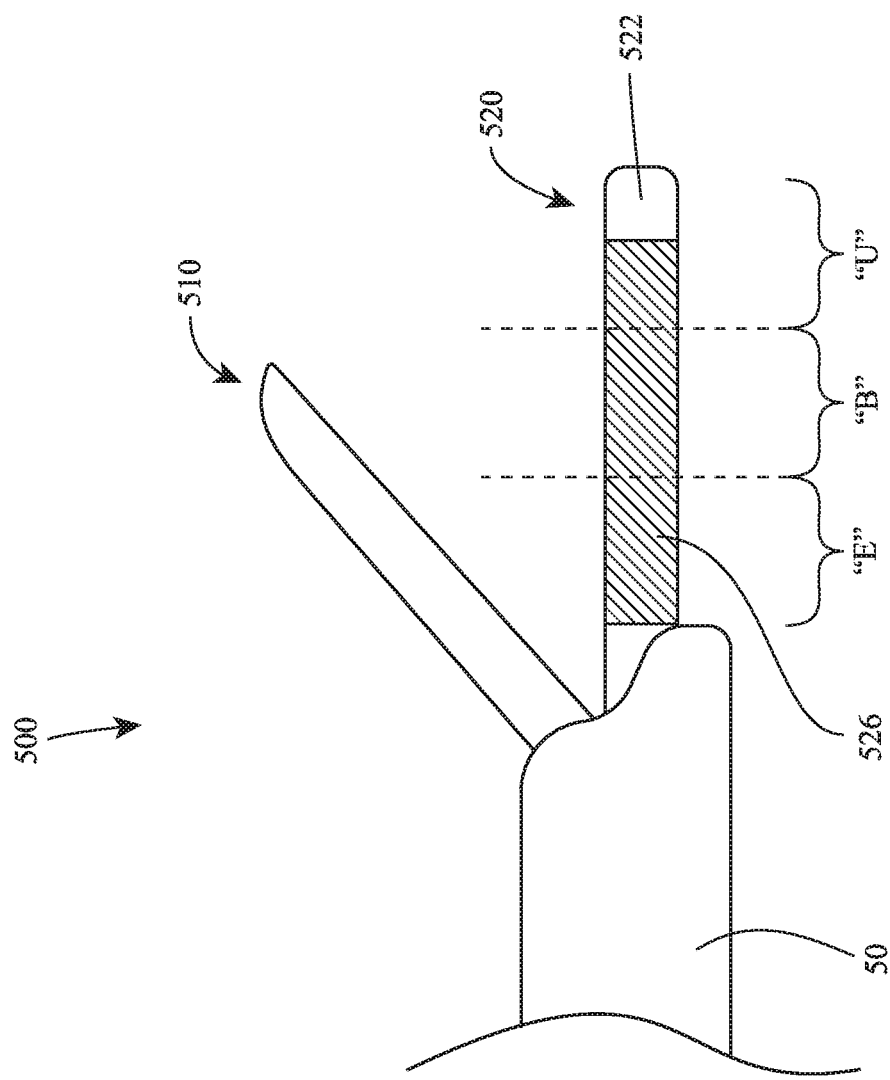
FIG. 3A is a longitudinal, cross-sectional view of yet another end effector assembly configured for use with the surgical instrument of FIG. 1.
Figure 3B:
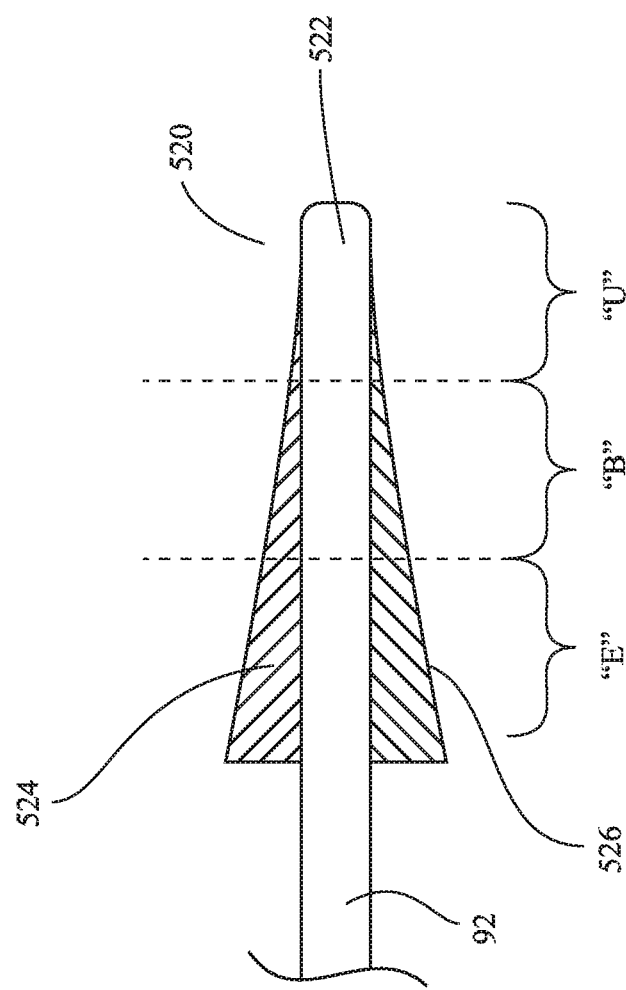
FIG. 3B is a top view of a second jaw member of the end effector assembly of FIG. 3A.

Referring now to FIGS. 3A-3B, in conjunction with FIG. 1, in accordance with another embodiment of the present disclosure, an end effector assembly is shown identified by reference numeral 500. End effector assembly 500 generally includes first and second jaw members 510, 520. First jaw member 510 may be configured similarly as first jaw member 410 of end effector assembly 400 (FIG. 2), including a jaw body (not shown) having a jaw liner (not shown) and first and second electrically-conductive tissue-contacting surfaces (not shown) disposed on either side of the jaw liner, although other configurations are also contemplated, e.g., jaw member may define an insulated tissue-contacting surface. The electrically-conductive tissue-contacting surfaces may be electrically coupled to one another or electrically isolated from one another, and may be energizable to the same or different potentials.

Second jaw member 520 includes an ultrasonic blade body 522 acoustically coupled to waveguide 92 and positioned to oppose the jaw liner of the first jaw member 510, and a pair of electrodes 524, 526 electrically coupled to generator 110 and activation switch 120, e.g., via one or more lead wires (not shown) extending through cable 100, housing 20, and elongated shaft 50. Electrodes 524, 526 extend along the majority of ultrasonic blade body 522 on opposing sides thereof and taper in thickness in the proximal to distal direction. Electrodes 524, 526 may be electrically isolated from one another to enable electrodes 524, 526 to be energized to different potentials and conduct energy therebetween, or may be electrically coupled to be energizable to the same potential for conducting energy to jaw member 510. The proximal portions of electrodes 524, 526, having relatively larger widths, conduct greater amounts of electrosurgical energy therebetween as compared to the distal portions of electrodes 524, 526, which have relatively smaller widths.

In use, electrosurgical energy delivery and ultrasonic energy delivery are activated simultaneously, in staggered but overlapping temporal relation, or consecutively. The ultrasonic energy is delivered from ultrasonic blade body 522 to tissue positioned between ultrasonic blade body 522 and the jaw liner of jaw member 510. The electrosurgical energy may be conducted transversely, wherein electrode 524 and the electrically-conductive tissue-contacting surface of jaw member 510 on the same side are energized to a first potential and electrode 526 and the electrically-conductive tissue-contacting surface of jaw member 510 on the same side are energized to a second, different potential, or may be conducted between jaw members 510, 520, wherein electrodes 524, 526 are energized to a first potential and the electrically-conductive tissue-contacting surfaces of jaw member 510 are energized to a second, different potential. In either configuration, due to the tapered configuration of electrodes 524, 526, upon activation, relatively more electrosurgical tissue treatment is effected in a proximal, electrosurgical treatment region "E" of jaw member 520, relatively more ultrasonic tissue treatment is effected in a distal, ultrasonic treatment region "U," and a blended treatment region "B" is disposed therebetween. As such, a clinician may position tissue within the electrosurgical treatment region "E," the ultrasonic treatment region "U," and/or the blended treatment region "B" to realize a desired result. The electrosurgical treatment region "E" may provide more robust sealing of tissue and greater seal widths which also improves seal quality, while the ultrasonic treatment region "U" may provide faster dissection of tissue. The blended treatment region "B" may provide moderate sealing and dissecting capabilities.

Figure 4A:
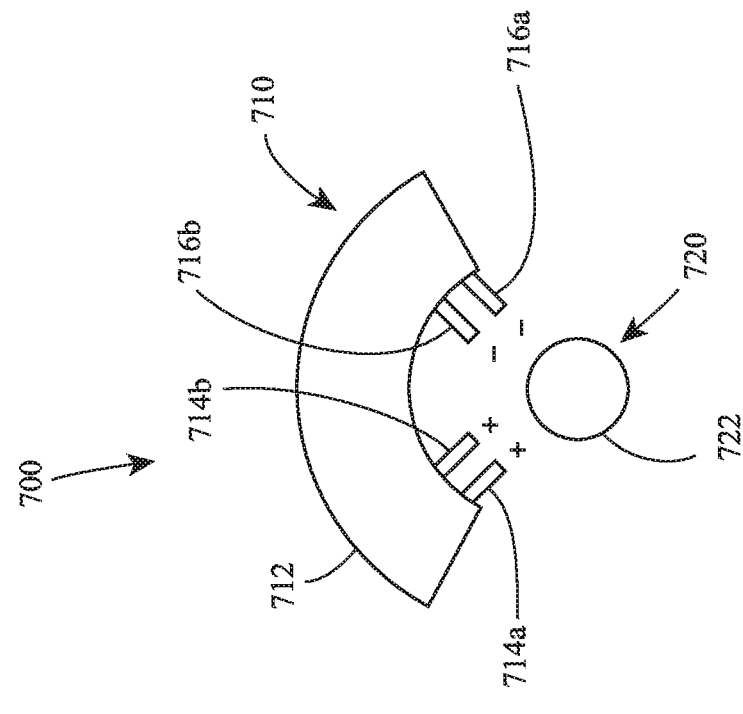
FIG. 4A is a transverse, cross-sectional view of another end effector assembly configured for use with the surgical instrument of FIG. 1, in a seal mode.
Figure 4B:
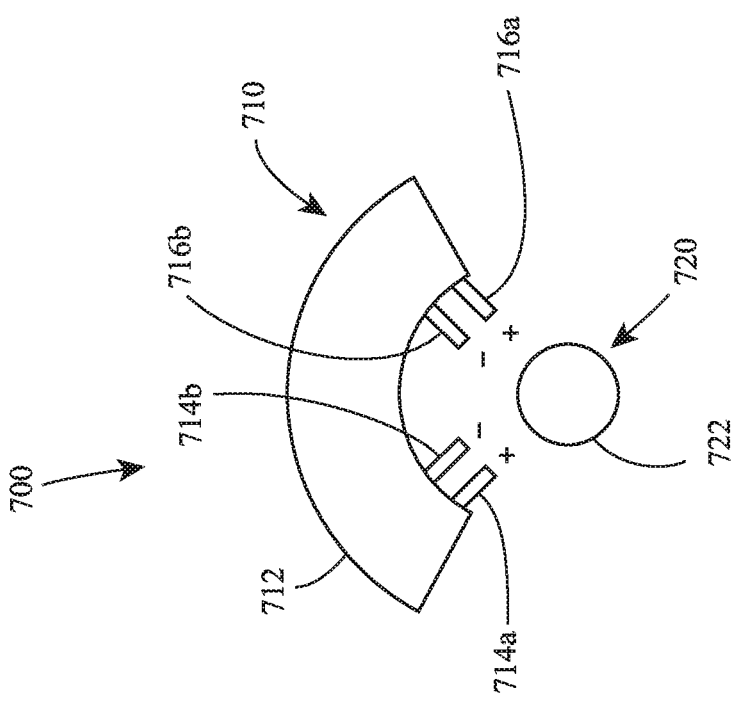
FIG. 4B is a transverse, cross-sectional view of the end effector assembly of FIG. 4A, in a dissection mode.

Referring now to FIGS. 4A and 4B, in conjunction with FIG. 1, an end effector assembly 700 in accordance with the present disclosure is shown. End effector assembly 700 generally includes a first jaw member 710 and a second jaw member 720. First jaw member 710 includes a jaw body 712 defining an arcuate configuration having first and second electrodes 714a, 714b arranged in a pair towards a first side of jaw body 712 and third and fourth electrodes 716a, 716b arranged in a pair towards a second, opposite side of jaw body 712. Electrodes 714a, 714b, 716a, 716b are electrically isolated from one another and each is electrically coupled to generator 110 and activation switch 120, e.g., via one or more lead wires (not shown) extending through cable 100, housing 20, and elongated shaft 50. Electrodes 714a, 714b, 716a, 716b are selectively energizable to various different potentials to achieve a desired configuration. For example, as shown in FIG. 4A, in a "tissue sealing mode," electrodes 714a, 716a may be energized to a first potential and electrodes 714b, 716b to a second, different potential such that two tissue seals may be formed on clamped tissue, one towards each side of jaw body 712. The middle, substantially unsealed portion of the clamped tissue is configured to receive ultrasonic energy (simultaneously, overlapping, or consecutively with the supply of electrosurgical energy) from jaw member 720, serving as an ultrasonic blade body 722, to dissect the tissue between the two seals.

As another example, as shown in FIG. 4B, in a "tissue dissecting mode," electrodes 714a, 714b may be energized to a first potential and electrodes 716a, 716b to a second, different potential such that currently flows transversely across jaw member 710 to facilitate dissection of tissue while ultrasonic energy (simultaneously, overlapping, or consecutively with the supply of electrosurgical energy) from jaw member 720 likewise effects dissection of tissue clamped between jaw members 710, 720. Other configurations are also contemplated.

Figure 5:
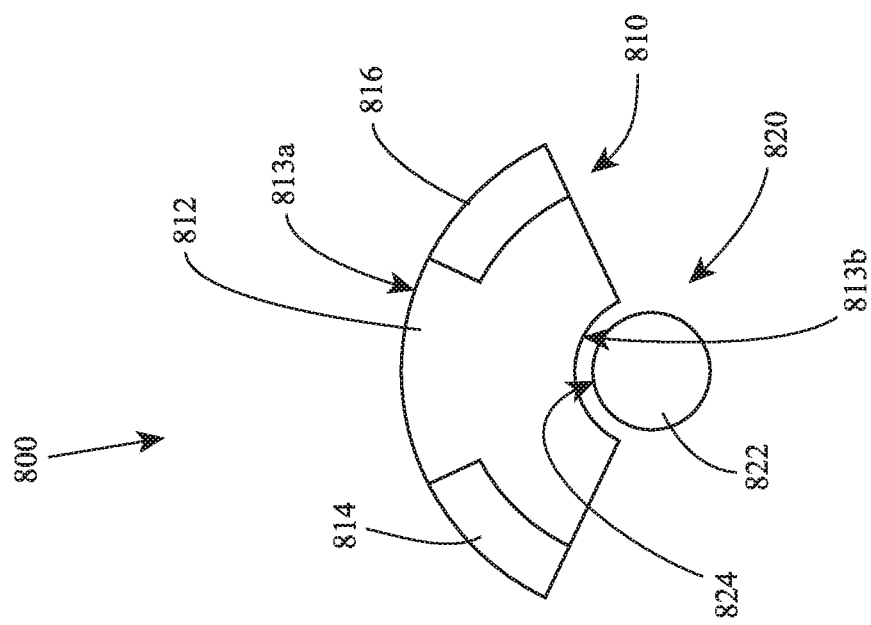
FIG. 5 is a transverse, cross-sectional view of yet another end effector assembly configured for use with the surgical instrument of FIG. 1.

Referring now to FIG. 5, in conjunction with FIG. 1, in accordance with another embodiment of the present disclosure, an end effector assembly 800 is shown. End effector assembly 800 generally includes first and second jaw members 810, 820. First jaw member 810 includes a jaw liner body 812 formed from or coated with an electrically-insulative material, which may be compliant, e.g., PTFE, and first and second electrodes 814, 816 disposed on jaw liner body 812. Jaw member 810, more specifically, defines a wedge-shaped configuration with an inwardly-facing tissue-contacting arcuate surface 813b, formed by jaw liner body 812, and an outwardly-facing arcuate surface 813a having a greater radius of curvature as compared to surface 813b. Electrodes 814, 816 define the end portions of outwardly-facing arcuate surface 813b, while jaw liner body 812 forms the middle portion of surface 813a. Jaw liner body 812 electrically isolates electrodes 814, 816 from one another, each of which are electrically coupled to generator 110 and activation switch 120, e.g., via one or more lead wires (not shown) extending through cable 100, housing 20, and elongated shaft 50.

Jaw member 820 serves as an ultrasonic blade body 822 and is also electrically coupled to generator 110 and activation switch 120, e.g., via one or more lead wires (not shown) extending through cable 100, housing 20, and elongated shaft 50. Ultrasonic blade body 822 may define an arcuate tissue-contacting surface 824 that is complementary to inwardly-facing tissue-contacting arcuate surface 813b of jaw member 810 to facilitate clamping tissue therebetween while maximizing surface area.

In operation, end effector assembly 800 may be activated in a first configuration, wherein ultrasonic energy is transmitted along waveguide 92 to jaw member 820 while electrodes 814, 816 are not energized, to enable treating tissue clamped between ultrasonic blade body 822 of jaw member 820 and jaw liner body 812 of jaw member 810. In a second configuration, end effector assembly 800 may be activated such that electrodes 814, 816 are energized to a first potential and jaw member 820 is energized to a second, different potential, such that electrosurgical energy is conducted through tissue clamped between jaw members 810, 820 to treat tissue. In a third configuration, electrodes 814, 816 are energized to different potentials and jaw member 820 remains electrically neutral such that electrosurgical energy is conducted transversely through tissue clamped between jaw members 810, 820 between electrodes 814, 816.

Figure 6:
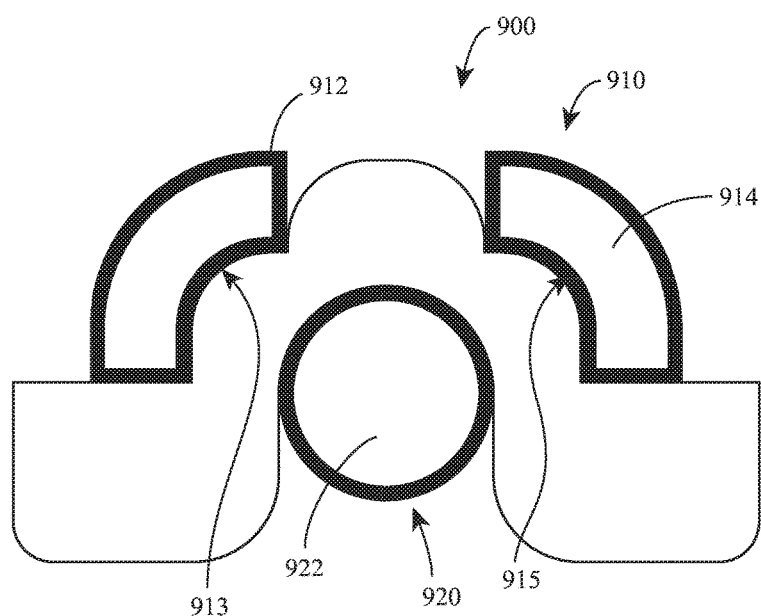
FIG. 6 is a transverse, cross-sectional view of still another end effector assembly configured for use with the surgical instrument of FIG. 1, shown clamping on tissue.

With reference to FIG. 6, in conjunction with FIG. 1, in accordance with another embodiment of the present disclosure, an end effector assembly 900 is shown. End effector assembly 900 generally includes a first jaw member 910 and a second jaw member 920. First jaw member 910 is bifurcated into jaw components 912, 914 that are spaced-apart and electrically isolated from one another. Jaw components 912, 914 are electrically coupled to generator 110 and activation switch 120, e.g., via one or more lead wires (not shown) extending through cable 100, housing 20, and elongated shaft 50, and may be energized to similar or different potentials.

Jaw member 920 is an ultrasonic blade body 922 that is acoustically coupled to waveguide 92 to enable transmission of ultrasonic energy from ultrasonic transducer 90, along waveguide 92, to ultrasonic blade body 922. Ultrasonic blade body 922 is also electrically coupled to generator 110 and activation switch 120, e.g., via one or more lead wires (not shown) extending through cable 100, housing 20, and elongated shaft 50, to enable ultrasonic blade body 922 to be energized with electrosurgical energy.

Ultrasonic blade body 922 defines a generally circular configuration. Jaw components 912, 914 define radiused tissue-contacting surfaces 913, 915, respectively, that generally conform to the curvature of ultrasonic blade body 922 of second jaw member 920, e.g., the radii of curvature of tissue-contacting surfaces 913, 915 generally approximate the radius of ultrasonic blade body 922 (wherein "generally" takes into account manufacturing, material, and other tolerances). However, other configurations are also contemplated.

In operation, trigger 40 is actuated to move jaw members 910, 920 to the approximated position to clamp tissue therebetween. With jaw members 910, 920 in the approximated position clamping tissue therebetween, jaw component 912, jaw component 914, and ultrasonic blade body 922 may define any suitable electrical configuration to achieve a desired tissue effect. For example, end effector assembly 900 may be activated: in a first configuration, wherein ultrasonic energy is transmitted along waveguide 92 to ultrasonic blade body 922 while jaw components 912, 914 are not energized; in a second configuration, wherein jaw components 912, 914 are energized to a first potential and ultrasonic blade body 922 is energized to a second, different potential; in a third configuration, wherein jaw components 912, 914 are energized to different potentials and ultrasonic blade body 922 remains electrically neutral; in a fourth configuration, wherein jaw components 912, 914 are energized to different potentials and ultrasonic blade body 922 is energized with ultrasonic energy but is otherwise electrically neutral; in a fifth configuration, wherein jaw components 912, 914 are energized to the same potential and ultrasonic blade body 922 is energized with ultrasonic energy and to a different electrical potential; etc.

Figure 7:
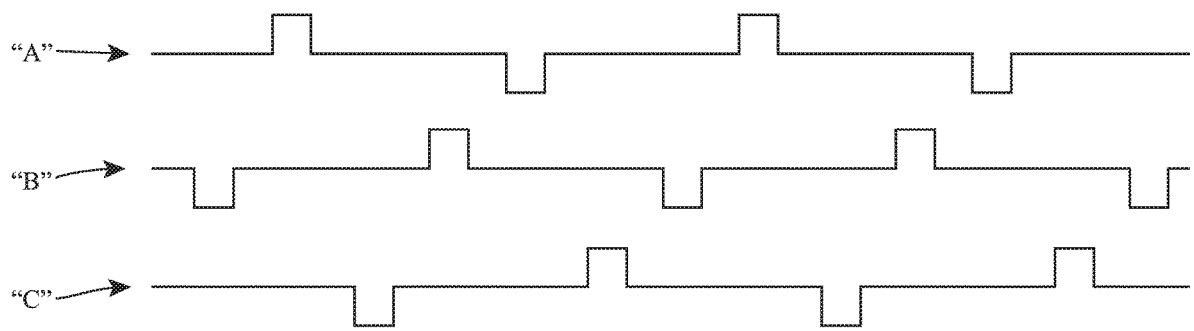
FIG. 7 is a graph illustrating a three-phase configuration for energizing three electrodes in accordance with the end effector assemblies of FIGS. 1, 5, and/or 6.

Referring to FIG. 7, in conjunction with FIGS. 1, 5, and 6, end effector assemblies 800, 900 (or any other suitable end effector assembly with at least three independently-energizable electrodes) are advantageous in that they allow for various different electrical configurations. In some electrical configuration, the three electrodes "A," "B," and "C" (corresponding to the three independently-energizable electrodes of a suitable end effector assembly) may be energized to a three-phase configuration, wherein each of the electrodes "A," "B," and "C" is energized with waves that are 120 degrees out of phase relative to each other such as, for example, as illustrated in FIG. 7. Although square waves are illustrated in FIG. 7, it is also contemplated that sine waves or other suitable waves that are 120 degrees out of phase relative to each other may also be provided.

A three-phase configuration such as that detailed above enables energy excitation between all three electrodes "A," "B," and "C." Further, the amount of energy supplied may be controlled such as, for example, by using square waves of less than 50% duty cycle. Additionally or alternatively, the amplitudes of any or all of the three phases may be controlled to produce more or less energy excitation in certain directions, e.g., between different combinations of electrodes "A," "B," and "C."

Regardless of the three-phase configuration utilized, ultrasonic energy may be supplied simultaneously, before/after, overlapping, alternating, during only portions of three-phase energy application, or in any other suitable manner, or may not be supplied during three-phase energy application. Likewise, the three-phase energy may be supplied simultaneously, before/after, overlapping, alternating, during only portions of ultrasonic energy application, or in any other suitable manner, or may not be supplied during ultrasonic energy application.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical instrument, comprising:
   an end effector assembly, including:
      a first jaw member; and
      a second jaw member including an ultrasonic blade body, the ultrasonic blade body defining an upper surface facing the first jaw member, a first lateral side and a second lateral side, the second jaw member including first and second electrodes disposed on the first lateral side and the second lateral side, respectively, of the ultrasonic blade body and extending longitudinally along a majority of a length of the ultrasonic blade body, the first electrode defining a first upper surface and the second electrode defining a second upper surface, the ultrasonic blade body adapted to receive ultrasonic energy, the first and second electrodes tapering in width proximally to distally and adapted to connect to a source of electrosurgical energy, wherein the first upper surface of the first electrode and the second upper surface of the second electrode are aligned with the upper surface of the ultrasonic blade body to define a substantially planar surface configured to contact tissue, wherein the first jaw member is movable relative to the second jaw member between a spaced-apart position and an approximated position for grasping tissue therebetween.

2. The surgical instrument according to claim 1, wherein the first and second electrodes are electrically-isolated from one another and energizable to different potentials for conducting electrosurgical energy therebetween.

3. The surgical instrument according to claim 1, wherein the first and second electrodes are electrically-coupled to one another and configured to conduct energy from the first and second electrodes to the first jaw member.

4. The surgical instrument according to claim 1, wherein the first jaw member includes a jaw liner disposed thereon and positioned to oppose the ultrasonic blade body of the second jaw member.

5. The surgical instrument according to claim 1, wherein the first jaw member includes first and second electrodes positioned to oppose the first and second electrodes, respectively, of the second jaw member.

6. The surgical instrument according to claim 5, wherein the first and second electrodes of the first jaw member are electrically-isolated from one another and energizable to different potentials for conducting electrosurgical energy therebetween.

7. The surgical instrument according to claim 5, wherein the first and second electrodes of the first jaw member and the first and second electrodes of the second jaw member are energizable to different potentials for conducting electrosurgical energy therebetween.

8. The surgical instrument according to claim 1, further comprising:
 a housing;
 a shaft extending distally from the housing; and
 an ultrasonic waveguide extending through the shaft, the ultrasonic waveguide configured to transmit ultrasonic energy to the ultrasonic blade body,
 wherein the end effector assembly is supported at a distal end portion of the shaft.

9. The surgical instrument according to claim 8, further comprising a trigger operably associated with the housing and coupled to the first jaw member, the trigger selectively actuatable to move the first jaw member relative to the second jaw member between the spaced-apart position and the approximated position.

10. The surgical instrument according to claim 8, further comprising an activation button disposed on the housing, the activation button selectively activatable to supply at least one of electrosurgical energy and ultrasonic energy to the end effector assembly.

11. The surgical instrument according to claim 10, wherein the activation button is selectively activatable to supply both electrosurgical energy and ultrasonic energy to the end effector assembly.

12. A surgical instrument, comprising:
 an end effector assembly, including:
  a jaw member;
  an ultrasonic blade body adapted to receive ultrasonic energy, the ultrasonic blade body defining an upper surface facing the jaw member, a first lateral side and a second lateral side, wherein the jaw member is movable relative to the ultrasonic blade body between a spaced-apart position and an approximated position for grasping tissue between the jaw member and an upper portion of ultrasonic blade body that opposes the jaw member in the approximated position thereof; and
  first and second electrodes disposed on the first lateral side and the second lateral side, respectively, of the ultrasonic blade body on opposite sides of the upper portion, the first and second electrodes tapering in width proximally to distally and adapted to receive electrosurgical energy, the first electrode defining a first upper surface and the second electrode defining a second upper surface,
 wherein the first upper surface of the first electrode and the second upper surface of the second electrode are aligned with the upper surface of the ultrasonic blade body to define a substantially planar surface configured to contact tissue.

13. The surgical instrument according to claim 12, wherein the first and second electrodes extend along a majority of a length of the ultrasonic blade body.

14. The surgical instrument according to claim 12, wherein the first and second electrodes are electrically-isolated from one another and energizable to different potentials for conducting energy therebetween.

15. The surgical instrument according to claim 12, wherein the first and second electrodes are electrically-coupled to one another and energizable to the same potential.

16. The surgical instrument according to claim 12, wherein the jaw member includes a jaw liner disposed thereon and positioned to oppose the upper portion of the ultrasonic blade body in the approximated position of the jaw member.

17. The surgical instrument according to claim 12, wherein the jaw member includes at least one electrode configured to enable conduction of energy between the at least one electrode and the first and second jaw electrodes.

18. The surgical instrument according to claim 12, further comprising:
 a housing;
 a shaft extending distally from the housing; and
 an ultrasonic waveguide extending through the shaft, the ultrasonic waveguide configured to transmit ultrasonic energy to the ultrasonic blade body,
 wherein the end effector assembly is supported at a distal end portion of the shaft.

* * * * *